(12) United States Patent
Kelly et al.

(10) Patent No.: US 8,038,937 B2
(45) Date of Patent: Oct. 18, 2011

(54) AUTONOMOUS DEVICE WITH BIOFOULING CONTROL AND METHOD FOR MONITORING AQUATIC ENVIRONMENT

(75) Inventors: Vincent M. Kelly, Easton, MD (US); Louis A. Codispoti, Oxford, MD (US); Jay Harford, Trappe, MD (US)

(73) Assignee: University of Maryland Center for Environmental Science, Cambridge, MD (US)

( * ) Notice: Subject to any disclaimer, the term of this patent is extended or adjusted under 35 U.S.C. 154(b) by 443 days.

(21) Appl. No.: 12/187,787

(22) Filed: Aug. 7, 2008

(65) Prior Publication Data

US 2009/0041621 A1    Feb. 12, 2009

Related U.S. Application Data

(60) Provisional application No. 60/954,412, filed on Aug. 7, 2007.

(51) Int. Cl.
*B08B 17/00*    (2006.01)
*B01J 19/00*    (2006.01)
(52) U.S. Cl. .................. 422/6; 422/40; 422/261
(58) Field of Classification Search ............... 422/6, 40, 422/261, 268, 275, 277, 900
See application file for complete search history.

(56) References Cited

U.S. PATENT DOCUMENTS

| | | | | |
|---|---|---|---|---|
| 4,089,209 A | * | 5/1978 | Grana et al. | 73/170.29 |
| 4,763,537 A | * | 8/1988 | Scott et al. | 73/170.29 |

\* cited by examiner

*Primary Examiner* — Walter Griffin
*Assistant Examiner* — Timothy Cleveland
(74) *Attorney, Agent, or Firm* — Rosenberg, Klein & Lee

(57) ABSTRACT

The device with biofouling control for monitoring aquatic (or gaseous) environment encloses an environmental sensor instrument in a sensor chamber which programmably opens for allowing direct communication between the sensors and the water of interest for sampling and which is closed after the sampling sequence is completed to create an anti-fouling environment in the sensor chamber by adding a biocide into the chamber and exposing the sensors to the anti-fouling environment for a predetermined period of time. The monitoring device includes a microprocessor which is preprogrammed prior to deployment of the device (and which may be re-programmed from a remote host computer during the deployment) into the aquatic environment and which controls the operation of the entire device for a long deployment (up to several months). The opening/closing of the sensor housing, instrument sampling and release of the biocide into the chamber are synchronized to provide the most effective sampling/anti-fouling sequence of operations of the autonomous device.

20 Claims, 12 Drawing Sheets

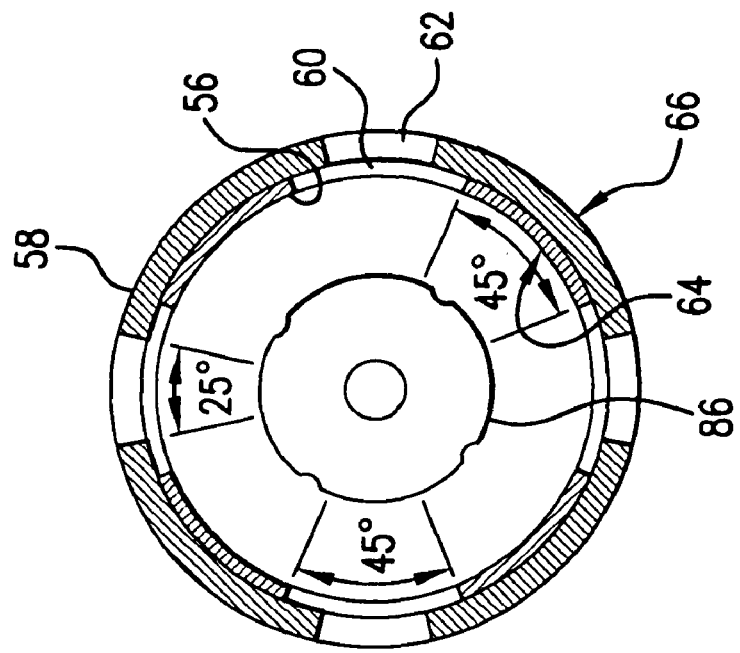
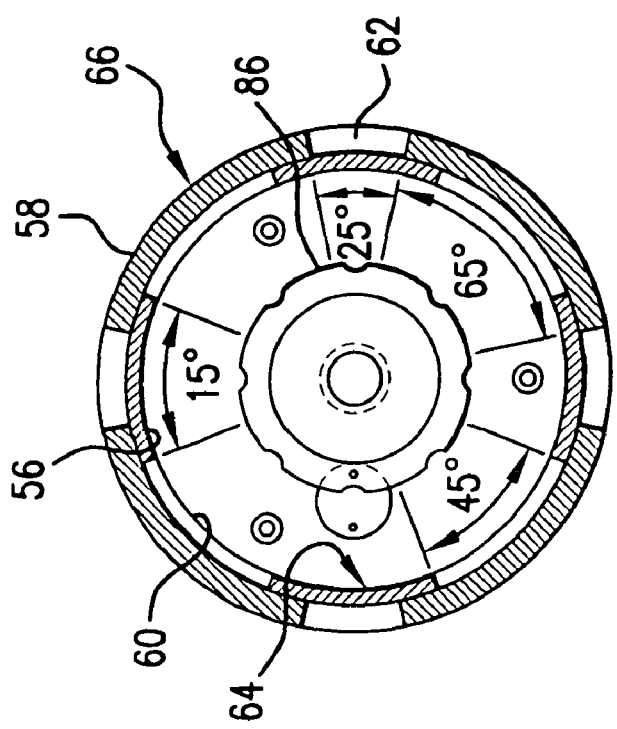
FIG. 8B
FIG. 8A

US 8,038,937 B2

AUTONOMOUS DEVICE WITH BIOFOULING CONTROL AND METHOD FOR MONITORING AQUATIC ENVIRONMENT

REFERENCE TO RELATED APPLICATIONS

The present Utility Patent Application is based on the Provisional Patent Application 60/954,412 filed 7 Aug. 2007.

FIELD OF THE INVENTION

The present invention is directed to the monitoring of fluid (aquatic and gaseous) environments, and more in particular to devices with anti-biofouling capabilities deployed in aquatic environment for acquisition of data related to chemical and physical conditions of the environment of interest.

In overall concept, the present invention is directed to biofouling control in device monitoring an aquatic environment by means of periodically exposing the deployed environmental sensor(s) to a biocide environment after sampling sequence is completed by the sensor(s), thereby protecting the immediate surrounding of the sensors from biofouling formation.

The present invention is further directed to an autonomous device which is preprogrammed prior to deployment in an aquatic environment of interest to operate in accordance with a predetermined sampling cycle in which during a sampling time period, the sensor samples water from the aquatic environment of interest. The sampling time period is followed by an anti-fouling treatment time period during which the immediate surrounding of sensor is filled with anti-fouling biocide uniformly dispersed therein. The preprogrammed controller (microprocessor) in the autonomous device controls operation of mechanical/electrical mechanisms of the autonomous device in synchronism with the sensors' sampling cycle and biocide release in the immediate surroundings of the sensors. Users can program the microprocessor prior to deployment of the autonomous device to control sampling frequencies, biocide dispense times and amounts, etc., as well as to permit communication of the autonomous device with a remote data acquisition system for an extended deployment.

BACKGROUND OF THE INVENTION

There is an ever increasing interest in the deployment of autonomous devices for monitoring chemical and physical conditions in aquatic environments. This interest encompasses monitoring fisheries, weather prediction, and global change in the open ocean. It also includes estuaries where interest arises from concerns about pollution, harmful algal blooms, living resources and biological diversity.

Reflecting the need for autonomously collected data, the advances in technology have produced reasonably affordable instrumentation capable of collecting and telemetering data. However, biofouling remains a major problem that to date has not been adequately addressed. The amount of growth that can accumulate in and around sensors over periods as short as two weeks can be great in high nutrient estuarine environments. Biofouling is, for a large percentage of instrumentation deployments, the single biggest factor affecting the operation, maintenance and data quality of in-water monitoring sensors, and therefore biofouling prevention for sensor systems is considered a major issue in aquatic environment monitoring.

The scientific community recognizes that not only sensors of monitoring devices must be protected from biofouling, but additionally the environment surrounding the sensors must also be protected since in some cases, fouling can become so extreme that one can question whether the sensors are sampling the ambient water or a microenvironment controlled by the activities of the fouling organisms.

The biofouling of ships and instrumentation is typically controlled through the use of toxic paints incorporating metal biocides, e.g. cuprous oxide, and organometals, e.g. tributaltine. Also, mechanical systems, such as anti-fouling wipers have been developed and used in multi-parameter monitor devices. However, the anti-fouling paints are extremely toxic and thus are harmful for living organisms, while wipers do not have the capability of complete prevention and removal of bio-fouling, thereby only partially addressing the bio-fouling problem. Such wipers also require additional energy consumption that is undesirable in autonomous devices.

Usually, deployed instrumentation is serviced once a week or biweekly (depending on a region and season) to remove deposits of bio-organisms from the sensors or to replace the deployed sensors with new ones. This is a time and cost consuming endeavor which makes aquatic environments monitoring extremely expensive and labor intensive.

There is therefore a need and ever increasing interest in monitoring of chemical and physical conditions in aquatic environments to provide autonomous devices capable of extended instrument deployment and of obtaining uncorrupted data by controlling the biofouling and eliminating the effect of biofouling on device operations.

SUMMARY OF THE INVENTION

It is therefore an object of the present invention to provide an extended deployment for devices monitoring aquatic environments with anti-fouling capabilities incorporated in the device.

It is another object of the present to provide a monitoring device with biofouling control for extended time operation in aquatic environments which is either preprogrammed prior to deployment or is controlled/re-programmed during the deployment from a remote host computer to perform sensor sampling cycles in which the sensor instrument samples the aquatic environment of interest for data acquisition. Subsequent to the sampling being completed, the sensor instrument is surrounded with a biocide anti-fouling environment to destroy and remove the fouling organisms from the environment immediately surrounding the sensor instrument.

It is a further object of the present invention to provide a sensor independent autonomous monitoring instrument in which the sensors are surrounded by a sensor envelope controlled in a predetermined fashion to permit communication of the sensor with the fluid of interest during a predetermined sampling time period followed by an anti-fouling treatment time period during which a biocide matter is dissolved within the sensor envelope to form an anti-biofouling environment in the immediate surroundings of the sensors.

It is an additional object of the present invention to provide a sensor within a chamber in which a biocide reservoir is disposed and controllably operated to release biocide salts into the sensor chamber after the sampling sequence has been completed, and wherein a preprogrammed controller actuates opening/closing of the sensor chamber to the aquatic environment in synchronism with a sampling cycle of the sensor and opening/closing of the biocide reservoir.

It is also an object of the present invention to provide a device with biofouling control for monitoring a fluid environment in which the sensor is positioned in a chamber and in which a control unit activates release of biocide matter from a biocide source in a controlled fashion through a density gradient mechanism to create an anti-fouling environment in the chamber.

The present invention, in one aspect thereof, is a device with biofouling control for monitoring a fluid (aquatic or gaseous) environment which includes one or several sensing units controllably operating in accordance with a predetermined sampling cycle composed of sampling time periods intermittent with the anti-fouling treatment time periods.

The device includes a sensor envelope (housing) surrounding the sensing units, a source of an anti-fouling biocide matter, and a control unit (preprogrammed microprocessor) which controllably opens the sensor envelope to create direct communication between the sensors and the fluid matter (water) of interest during the sampling time period, and which further closes the sensor envelope and "instructs" the biocide source to release the biocide matter to create an anti-biofouling environment in the sensor envelope during the anti-fouling treatment time periods.

Preferably, the source of biocide matter is a reservoir containing the biocide matter and a tube in controllable communication with the water of interest within the chamber surrounding the sensors. During the anti-fouling treatment time periods, the biocide matter gradually dissolves in the water of interest within the sensor envelope and forms an anti-biofouling environment around the sensors through a density gradient mechanism.

The sensor envelope is preferably formed as a housing with one or several windows which are controllably opened/closed in accordance with the sampling cycle of the sensors. The housing may be implemented as a double-wall structure having an outer cup and an inner cup positioned in concentric relationship each with the other and each having a plurality of openings of predetermined dimensions, and positioned at predetermined positions on the walls of the inner and outer cups. The controller changes a relative disposition between the inner and outer cups in synchronism with the sampling cycle of the sensors in order to control the relative disposition between the openings on the walls of the inner and outer cups, thereby controlling the extent of "openness/closeness" of the chamber to the aquatic environment.

The device further comprises an actuator unit operatively coupled to either the inner or outer cups to establish a respective relationship therebetween in accordance with the predetermined sampling cycle of the sensing unit(s) under the control of the microprocessor.

The data collected during the sampling periods are written into a nonvolatile memory in the autonomous device and may be periodically dispatched telemetrically, if needed, to a remote data acquisition system for further analysis and processing.

The parameters, such as sampling frequency, biocide dosing frequency (amount), etc., as well as a sequence of operations in the autonomous device, may be embedded into the microprocessor in a laboratory prior to deployment of the monitoring device or a remote control/re-programming may be provided from a remote host computer during the deployment. The microprocessor controls the sampling cycle of the sensors, as well as relative disposition of the inner and outer cups, in synchronism with the biocide release, collects data in the nonvolatile memory, and is further capable of processing the acquired data. A telemetry and data collection system may periodically request instrument data stored on the device's nonvolatile memory. Such data could then be displayed on the Internet for sharing the data with parties interested in such data receipt.

The device also includes a casing for accommodating mechanical/electrical parts and batteries, as well as for receiving a printed circuit board with electronics necessary for operation of the device.

The present invention further encompasses a method for biofouling control of an autonomous device for monitoring a fluid environment. The method comprises the following steps:

positioning a sensing unit into a chamber defined by a sensor envelope, operating the sensing unit in accordance with a predetermined sampling cycle having a sampling time period followed by an anti-fouling treatment time period, during the sampling time period, opening the chamber to the fluid environment to maintain fluid communication between the fluid matter of interest and the sensing unit, and sampling the fluid matter of interest during the sampling time period, during the anti-fouling treatment time period, closing the chamber upon completion of the sampling by the sensor unit, and releasing the biocide matter (or several biocide matters) in the chamber to create an anti-fouling environment therein to expose the sensor(s) to the anti-fouling environment. Preferably, when the biocide matter is controllably released in the chamber, the anti-fouling environment is stirred to evenly dispense the biocide matter within the chamber.

Further, upon completion of the anti-fouling treatment time period, opening the chamber, and replacing the anti-fouling environment in the chamber with the fluid matter of interest for the next sampling.

In the method of the present invention, a controller (microprocessor) may be preprogrammed prior to deployment so that the deployed autonomous monitoring device operates in accordance with the program and operational parameters "embedded" in the microprocessor for an extended deployment period. Alternatively, the monitoring device may be controlled/re-programmed during the deployment from a host computer.

The following operations are also generally important for operation of the monitoring device in question:

sampling the water by sensors during sampling time intervals and writing the data onto nonvolatile memory within the autonomous device;

when needed, establishing a communication link between the autonomous device and a remote computer system, and telemetrically sending the collected data from the memory to the remote computer system for further processing and analysis of the collected data.

These and further objects of the present invention will become evident in view of further disclosure taken in conjunction with accompanying Patent Drawings.

BRIEF DESCRIPTION OF THE DRAWINGS

FIGS. 8A and 8B show schematically a cross-section of interrelated inner and outer cups with the chamber completely closed (FIG. 7A) and open (FIG. 7B);

BRIEF DESCRIPTION OF THE PREFERRED EMBODIMENTS

Figure 1:
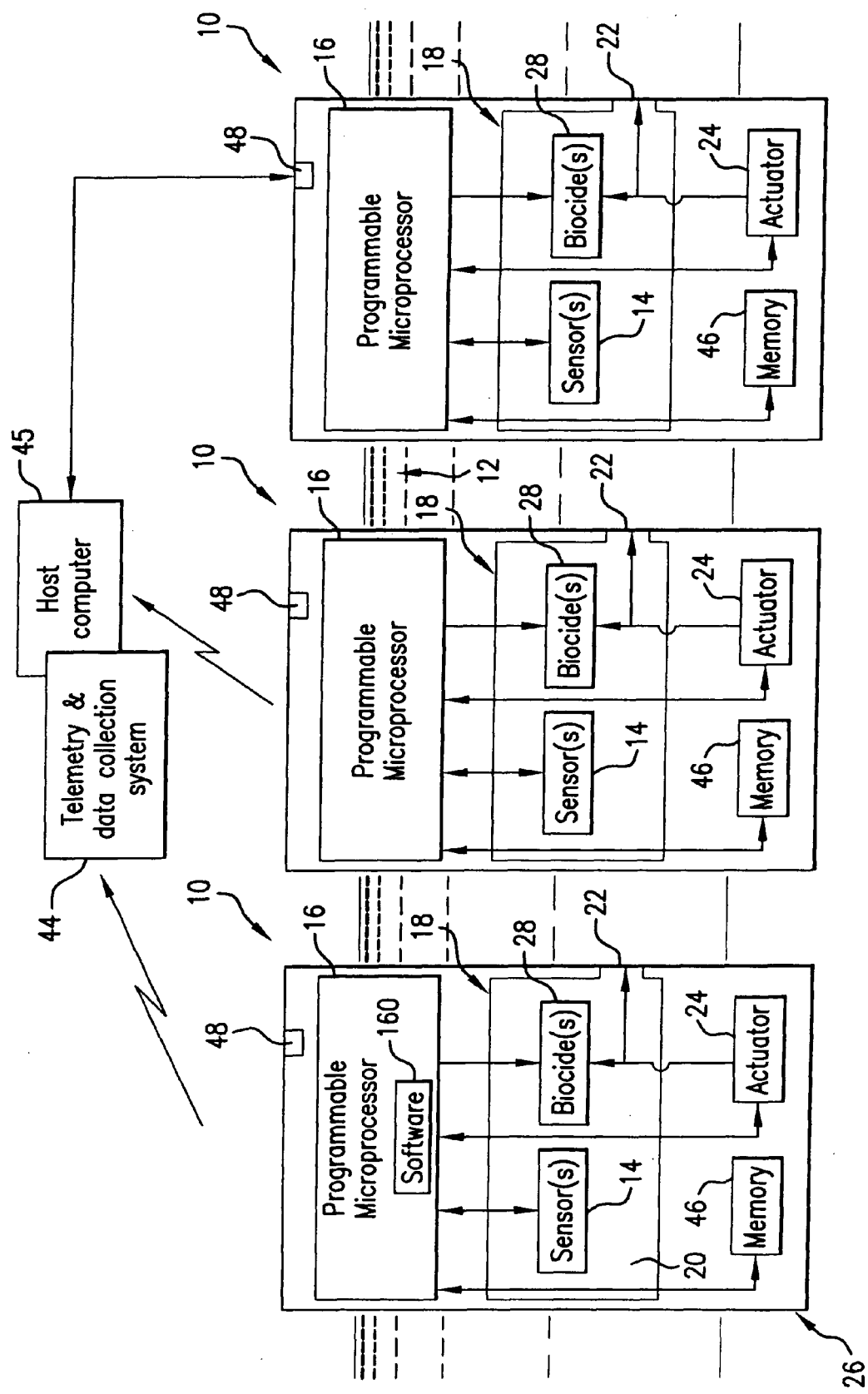
FIG. 1 is a schematic representation of monitoring devices of the present invention deployed for monitoring the environment of interest.

Referring to FIG. 1, a device 10 is shown with biofouling control for monitoring fluid environment (for example aquatic environment or gaseous environment) 12 is designed for deployment at a predetermined position in an aquatic environment for an extended period of time. Due to the anti-fouling control, the device 10 is capable of autonomous operation without the need for servicing more than once every two months.

The autonomous device 10 of the present invention may use any number of sensors 14 of a variety of types and is adapted to protect analog or serial sensors for measuring physical and chemical parameters of the water in the aquatic environment 12. As one of many possible examples, a multi-probe sensor instrument may be used with the autonomous device 10 of the present invention, such as multi-parameter Sondes YS16600 for monitoring dissolved oxygen, chlorophyll, blue-green algae, turbidity, temperature, pH level, etc., although other sensing arrangements are contemplated as well in the scope of the present invention.

Since the autonomous device 10 is deployed for significantly long periods of time, it is preferred that the sensors do not sample the water continuously but operate in accordance with a predetermined sampling cycle which is programmed into the microprocessor 16 of the autonomous device 10, prior to the deployment of device 10. For example, with the YS16600 multiprobe, the autonomous device 10 may sample water every 15 minutes which is generally regarded as a sufficiently high sample frequency for moored water quality sensors. Other sampling frequencies are envisioned subject to a specific requirement for monitoring the water.

The novel approach devised for anti-fouling control of the autonomous device 10 encompasses the enveloping of the environmental probes (sensors) 14 into a sensor envelope 18 to form a chamber 20 where a concentrated antifouling environment is periodically created to immediately surround the sensors between sampling periods. The sensor envelope 18 may be implemented in various alternative embodiments. As one of the alternative implementations, the sensor envelope 18 includes windows, or shutters, 22 which may be opened and closed via the control of an actuator 24, preferably a DC motor, contained in the electronics and battery housing 26, as will be disclosed in detail in further paragraphs.

Sampling cycles of the sensors 14 include sampling time periods followed by anti-fouling treatment time periods. During a sampling cycle, the shutters 22 are opened, the treated water of the previous cycle is flushed out with a stirrer, while new volume of water enters and fills the sensor envelope. The sensors 14 are instructed by the microprocessor 16 to start sampling during the sampling time period. Upon completion of the sampling, the shutters start closing and "dosing" of the water enclosed in the chamber 20 with one or more biocides 28 begins. The biocide(s) preferably is (are) delivered in a controlled manner via a density gradient pump mechanism as will be disclosed in further paragraphs, although other alternative mechanisms for controlled delivery and dispersion of biocide salt(s) in the sensor envelope is contemplated in the present device 10.

Figure 2:
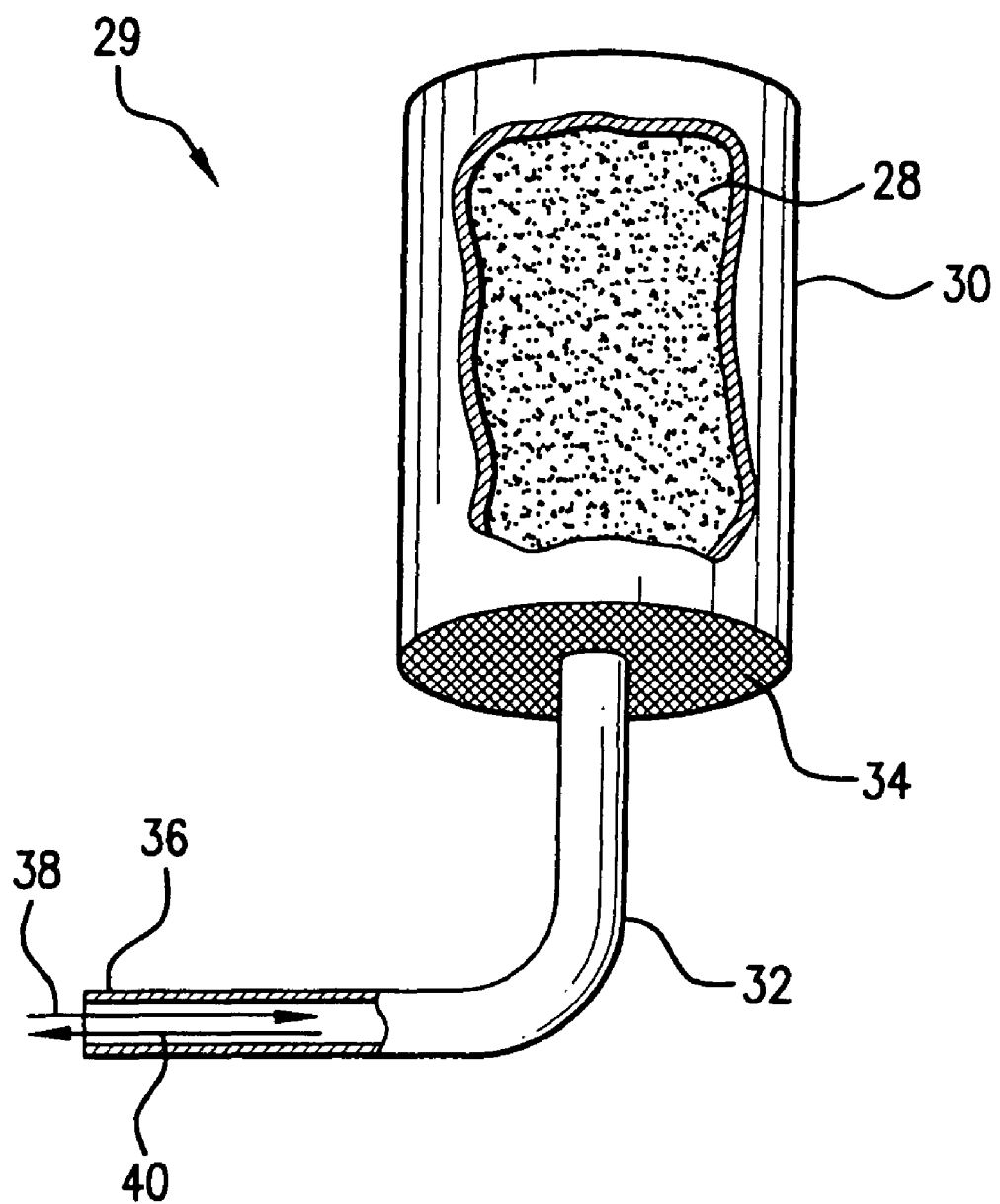
FIG. 2 is a schematic representation of the density gradient pump (biocide reservoir) in the device of the present invention.

As shown in FIG. 2, the density gradient pump 29 may be implemented as a reservoir 30 containing a dry salt, e.g. a biocide 28, that has a connection to the ambient water in the chamber 20 through a silicon tube 32 extending from the bottom of the biocide reservoir 30. The biocide 28 may include calcium hypochlorite pellets or powder, or copper chloride, salts of acids, various metal salts, and basically a very wide range of dry and water soluble chemicals for chamber 20 sterilization.

Additionally, the reservoir 30 is provided with a screen filter 34 on the bottom thereof which is added to suspend the dry biocide and to prevent small particulates from entering the tube 32 to avoid clogging of the tube and stoppage of the flow.

When the tube end 36 is opened, the reservoir 30 fills with raw natural water from the chamber 20 such that a concentrated and dense solution forms in the reservoir through the dissolution of a small fraction of the salt inside. When the connection to ambient water is open (tube end 36 is open), density driven flow develops in the tube 32 with the saturated salt solution below the lighter ambient water layer. As ambient water enters the reservoir as shown in FIG. 2, by the water flow 38, biocide salt is dissolved in the reservoir until there is saturation. The upper layer of water with the dissolved salt 40 flows from the reservoir to the ambient water in the chamber 20 down the tube end 36. This process continues until all the biocide is dissolved and the densities of the solution in the reservoir and ambient water are nearly equal. By using the ambient water in the chamber 20 to dilute a concentrated biocide 28 in the reservoir 30 and a density flow which drives the introduction of biocide into the chamber 20, the space and energy requirements for the operation of the autonomous device 10 are minimized.

The device 10 regulates biocide dosing into the chamber 20 using a cam actuated valve mechanism 42 shown in FIGS. 5, 6, 9A-9B, 10-13, 14A-14B, and described in detail in further paragraphs. The operation of the valve mechanism 42 is controlled by the actuator 24 in synchronism with opening/closing of the shutters 22 of the chamber 20. As will be presented further, when the shutters 22 in the chamber 20 are nearly closed, the valve mechanism 42 will gradually open the tube end 36 of the silicon tube 32 for a programmed duration. When the open tube end period expires, the shutters 22 in the chamber 20 move to the completely closed position thereby closing the tube end 36. The anti-fouling environment within the chamber 20 is then stirred briefly to evenly disperse the biocide inside the sensor envelope 18, e.g. in the chamber 20. It is contemplated in the scope of the present invention, that the autonomous device 10 may accommodate more than one biocide source, e.g., up to four different reservoirs 30 with different biocide salts.

The controller (microprocessor) 16 may be preprogrammed prior to deployment of the autonomous device 10 to control operation of the autonomous device 10. The microprocessor 16 also supervises serial communication of the autonomous device 10 with a telemetry and data collection system 44, to periodically dispatch data thereto when and if needed. Alternatively, the microcontroller 16 may be remotely controlled/re-programmed from a host computer 45, shown in FIG. 1, during the deployment of the device 10.

The deployment parameters including sampling frequency, biocide dosing frequency, as well as biocide dispense time and amount, stirring/flushing duration, as well as sequence of operations, are preferably embedded in the microprocessor 16 in a lab prior to deployment of the autonomous device 10. Thus, the autonomous device 10 independently controls the operation of the sensors 14, as well as the mechanics and electrical components. The microcontroller 16 further is "responsible" for data recording in the memory 46, and for synchronization of all the components operations over greater than two months deployment. The operation of the sensors 14, as well as the overall operation of the device 10, including the deployment parameters, also may be remotely reprogrammed during the deployment of the autonomous device 10.

The telemetry and data collection system 44 can periodically request the data stored on the non-volatile memory 46 of the autonomous device 10. A serial user interface 48, shown in FIG. 1, may be used in the autonomous device 10 to accommodate telemetered control and data acquisition.

It is clear that the device 10 is adapted for providing a continuous on-line external telemetry and ability of being remotely controlled and re-programmed during the deployment when in communication with the remote host computer 45, in addition to the autonomous operation of the device 10 which may run independently for as long as it is intended, by programming the microcontroller 16 before deployment. When pre-programmed prior to the deployment, the device 10 constitutes an independently controlled device which can operate autonomously without external control for extended time deployment periods.

Figure 3B:
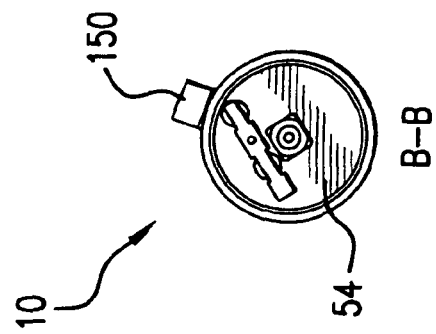
FIG. 3B is a side view taken along lines B-B of FIG. 3A.
Figure 3A:
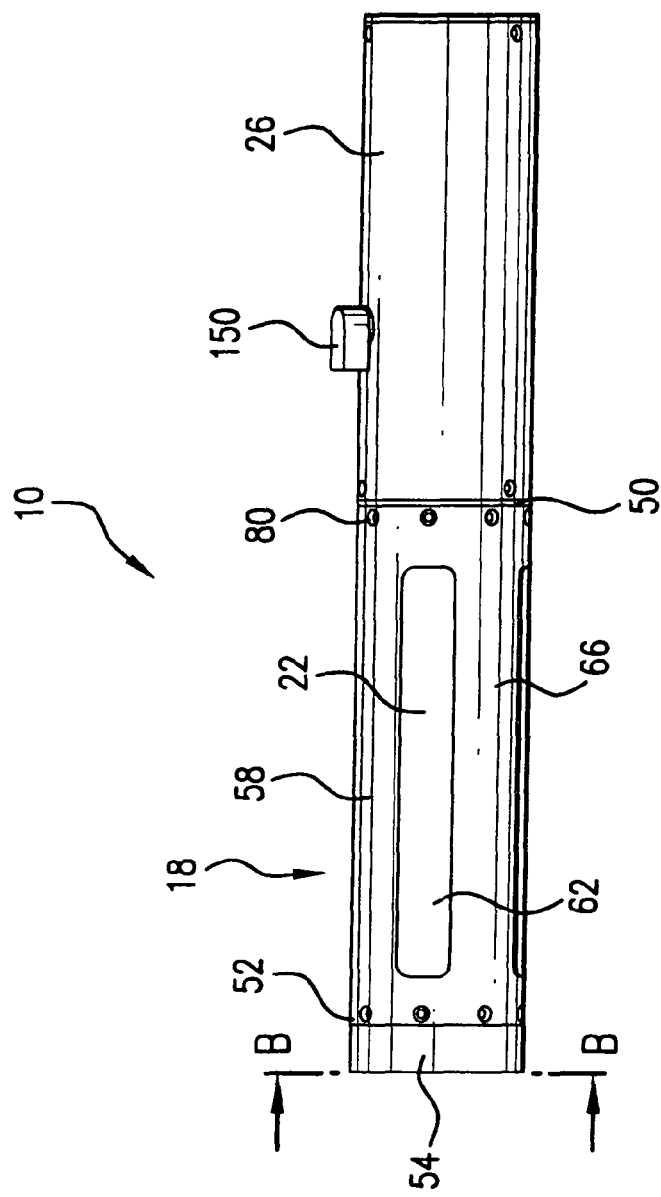
FIG. 3A is a representation of the monitoring device of the present invention.

Referring to FIG. 3A-3B, the autonomous device 10 includes the sensor envelope (housing) 18 coupled at an end 50 thereof with the electronics and battery housing 26. The sensor envelope 18 is adapted at the end 52 thereof to accommodate the sensor instrument 54 which has individual sensors 14 and which may be a single probe or a multiprobe environmental sensing instrument, such as for example 6-series sensors, which may be fitted into the sensor housing 18 which may have an annular cross-section shown in FIG. 3B.

Figure 6:
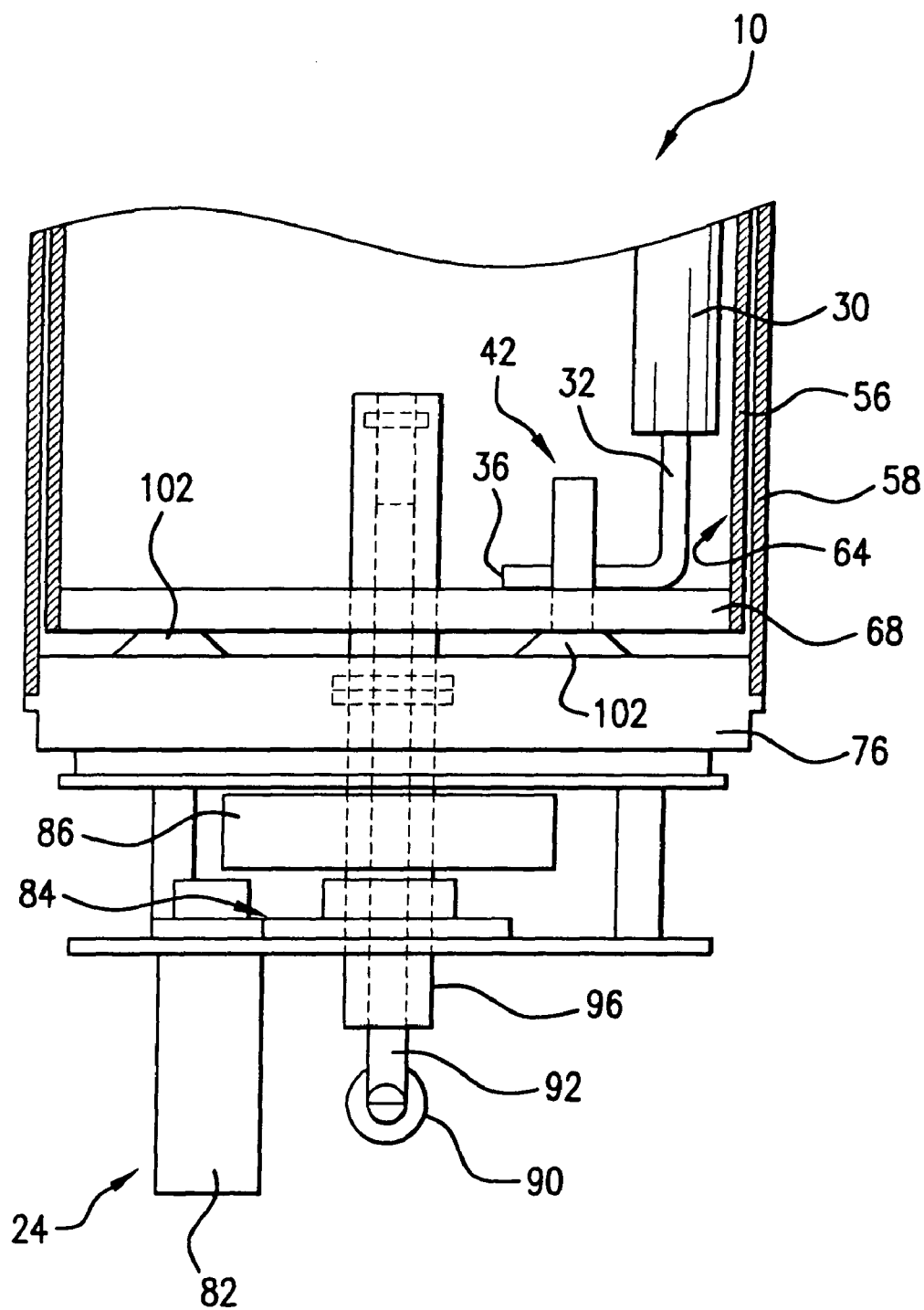
FIG. 6 is a further schematic representation of the mechanical control of the inner/outer cups motion and biocide release.
Figure 7:
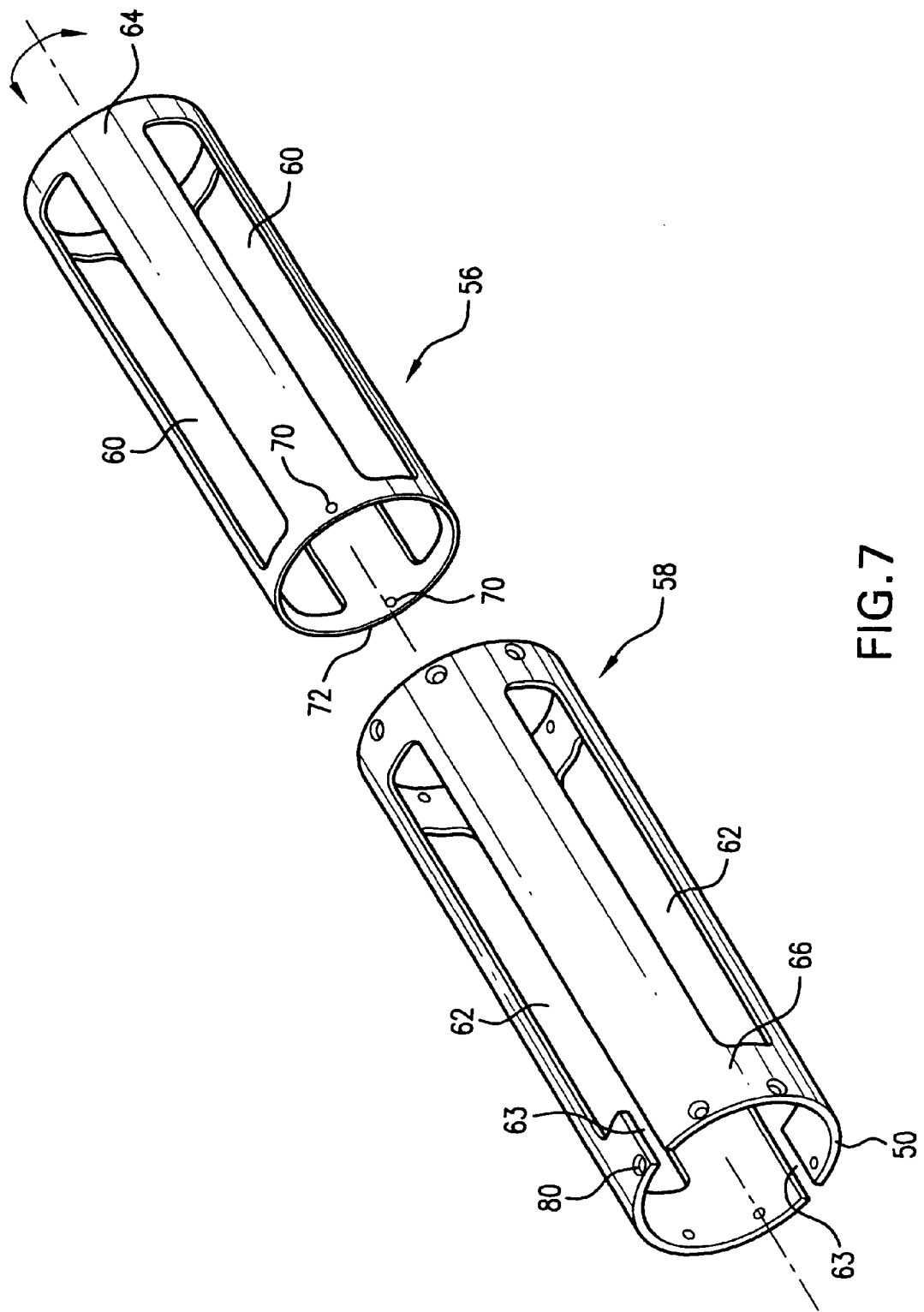
FIG. 7 is an expanded view of the interrelated inner and outer cups.
Figure 9A:
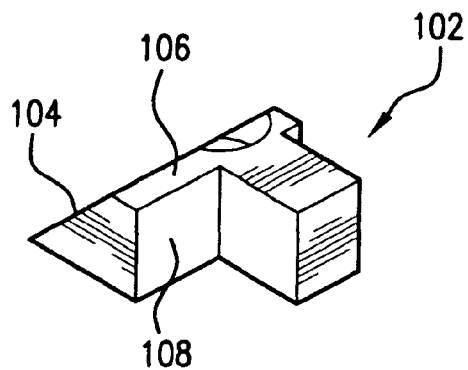
FIGS. 9A and 9B represent two perspective views of a ramp unit used for control of the biocide release.
Figure 9B:
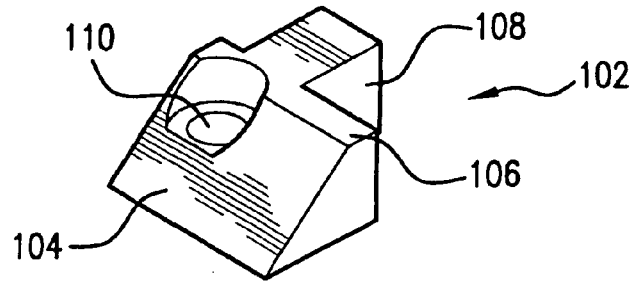
Figure 10:
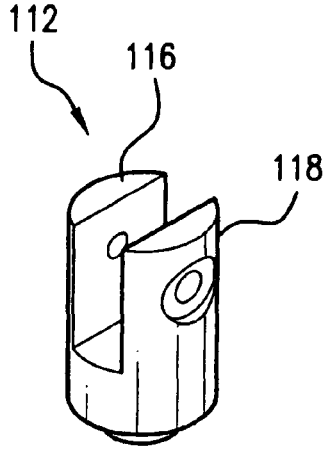
FIG. 10 is a perspective representation of the pivot post for control of the biocide release.
Figure 11:
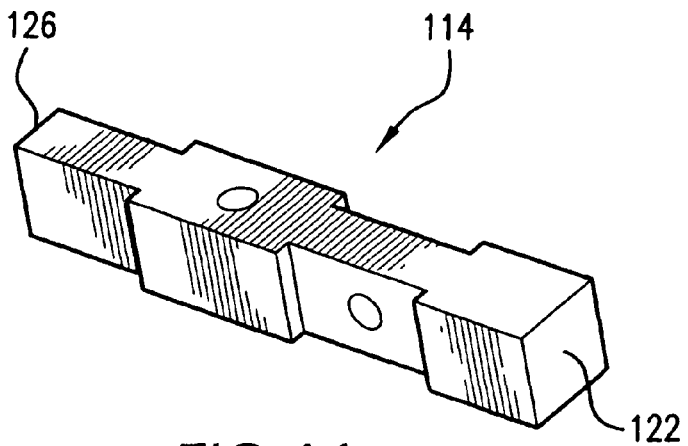
FIG. 11 is a perspective representation of the lever arm in the mechanism for control of the biocide release.
Figure 12A:
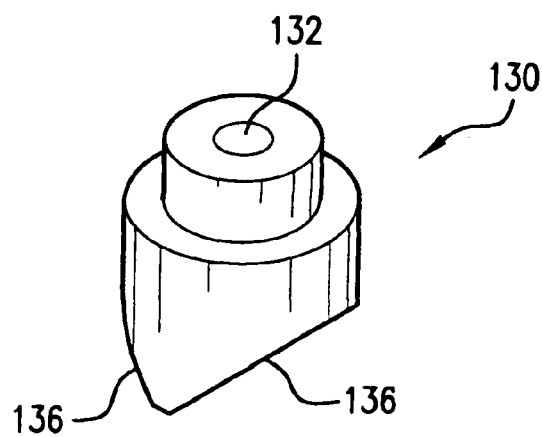
FIGS. 12A and 12B are two perspective representations of the pinch tip of the valve for controlling the release of the biocide.
Figure 13:
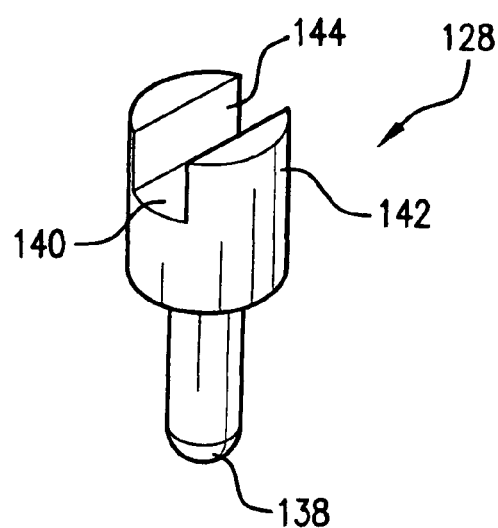
FIG. 13 is a perspective representation of the push rod of the mechanism for control of the release of the biocide.
Figure 12B:
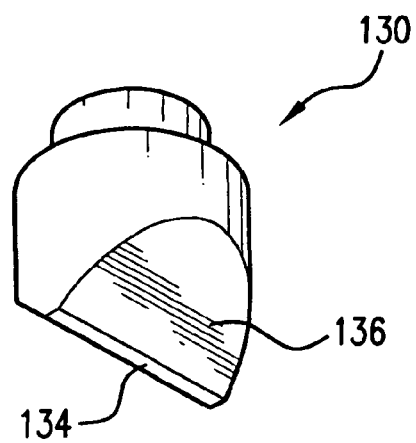

Although other implementations are contemplated in the present invention, as an example, the sensor housing 18 may be devised as a two-layer structure, which, as best shown in FIGS. 3A, 4, 6, 7 and 8A-8B, which includes an inner cup 56 and an outer cup 58 disposed concentrically each with respect to the other. The inner cup 56 has a plurality of inner cup openings 60, while the outer cup 58 has a plurality of outer cup openings 62 which correspond in shape and dimension to the inner cup openings 60. As shown in FIG. 7, although there are four inner cup openings 60 and four outer cup openings 62 on each respective cup 56 and 58, a different number of openings also may be contemplated in the scope of the present invention. The inner cup openings 60 and outer cup openings 62 are formed in the wall 64 of the inner cup 56 and of the wall 66 of the outer cup 58, respectively and at predetermined positions which are selected in correspondence each to the other.

In operation, when the water from the aquatic environment is to enter into the chamber 20, the actuator 24 (shown in FIGS. 1 and 4-6) rotates the inner or outer cups relative each to the other to align the inner cup opening 60 to the outer cup opening 62 in order to open the chamber 20 to the ambient aquatic environment. However, when the chamber 20 is to be closed, or partially closed, the actuator 24 rotates the inner or outer cups relative each to the other to controllably change the extent of overlapping between the inner cup opening 60 and outer cup opening 62 to either leave small openings in the chamber 20 or completely close the chamber by overlapping the inner cup openings 60 with the wall 66 of the outer cup between the openings 62.

Figure 4:
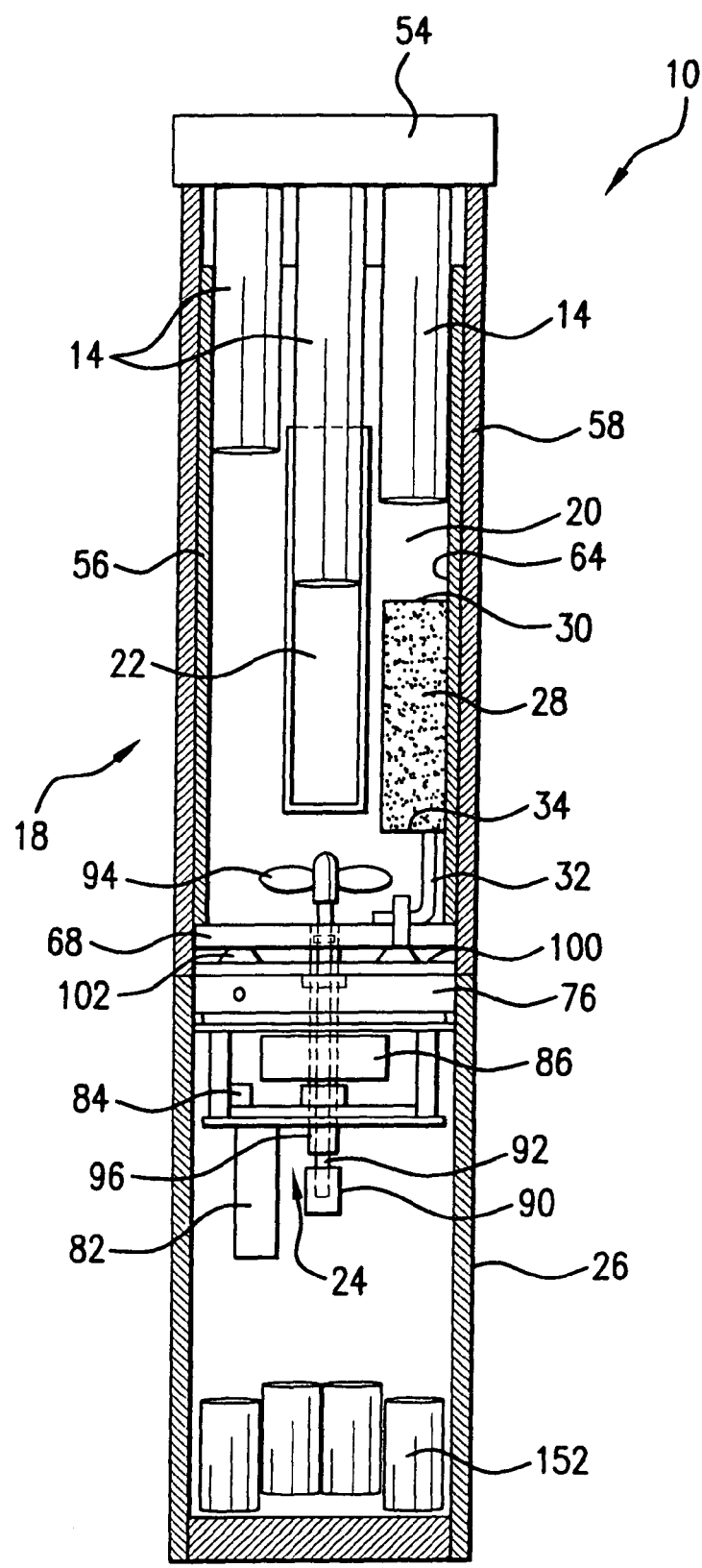
FIG. 4 is a longitudinal cross-section of the monitoring device of the present invention.
Figure 5:
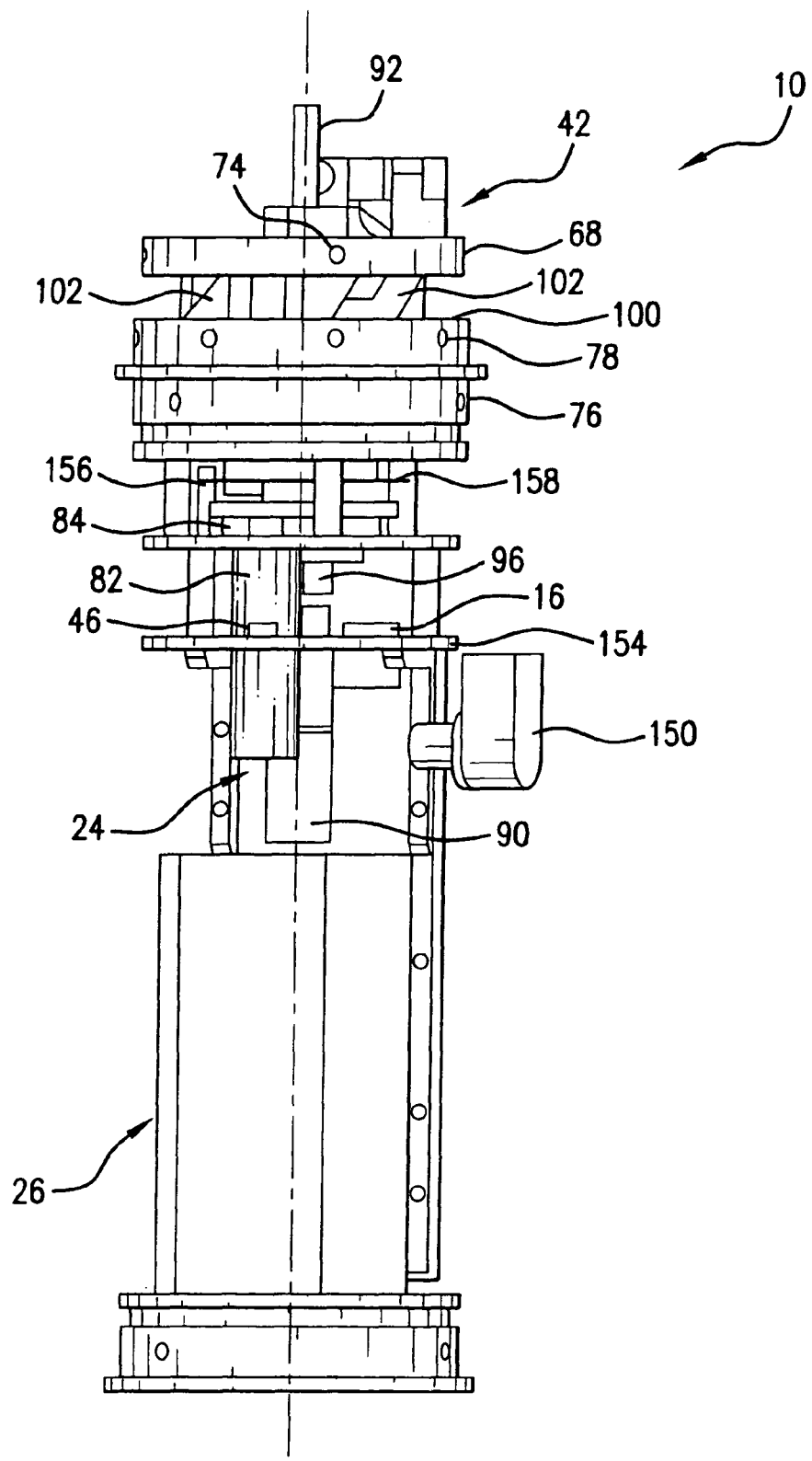
FIG. 5 is a schematic representation of the mechanical/electrical control mechanism and electronics in the device of the present invention

As best shown in FIGS. 4 and 6, the inner cup 56 is mounted to a support disk 68 by means of fasteners protruding through holes 70 formed at the edge 72 of the inner cup 56 (best shown in FIG. 7) and the openings 74 formed at the support disk 68 (best shown in FIG. 5). The outer cup 58 is mounted to the chamber bulk-head 76 (best shown in FIGS. 5 and 14A-14B) which has openings 78 positioned circumferentially around the perimeter thereof in alignment with the openings 80 at the edge 50 of the outer cup 58 as best shown in FIGS. 3A and 7.

The actuator 24 includes a motor 82 shown in FIGS. 4-6, which rotates the support disk 68 (e.g. the inner cup 56) through a gear mechanism 84 and a system of limit switch cams 86, schematically shown in FIGS. 4, 6 and 8A-8B. The support disk 68 is rotated in accordance with instruction received by the motor 82 from the programmable microprocessor 16. When the support disk 68 is rotated by the motor 82 through the gear mechanism 84 and the limit switch cams 86, the inner cup 56 mounted thereon also rotates relative to the outer cup 58 which remains immovable. In accordance with instructions received by the motor 82 from the programmable microprocessor 16, and as best shown in FIGS. 8A and 8B, the inner cup 56 may be displaced to a position relative to the outer cup 58 so that either the inner cup openings are disaligned with the outer cup openings, e.g. the openings are covered by the walls of the other cup, as shown in FIG. 8A. Alternatively, the inner cup openings and outer cup openings may be aligned each with respect to the other for complete opening of the chamber 20, as shown in FIG. 8B. There are other relative dispositions possible (although not shown), when there is a partial overlap between the openings and walls of another cup, to leave narrow slits opened in the sensor envelope to regulate flow of the water through the openings.

The actuator 24 may also have another motor 90 positioned on a stirrer shaft 92 which has a stirrer 94 (shown in FIG. 4) at the other end thereof. Alternatively, the motor 82 may perform the function of both rotating the inner cup, as well as the function of rotating the stirrer 94 by using a gear train between the motor 82 shaft and the stirrer shaft 92. For the single motor implementation, the mechanical component is changed, as well as the program "sewn-in" the microprocessor adjusted to specify an alternative schedule of operation. The stirrer shaft 92 passes through the cup rotator shaft 96, as best shown in FIGS. 4 and 6. The cup rotator shaft 96 is coupled to the gear mechanism 84 and is directly rotated by the motor 82 through the gear mechanism 84 and the limit switch cams 86.

Alternatively to cams and limit switches 86, an optical quadrature encoder 156, shown in FIG. 5, may be used to "count" the position of the motor 82 in order to control its motion action for rotational displacement of the inner/outer cups. The optical encoder 156 may be disposed in proximity to an encoder disk 158 which is attached to the inner cup shaft 96 to count the number of slits on the encoder disk 158. The "reading" is processed in the encoder 156 or in the microprocessor 16 which controls the motor 82 accordingly. Thus, the microcontroller 16 controls the inner cup motion (or relative disposition between the inner and outer cups) via navigation of the encoder 156.

Figure 14A:
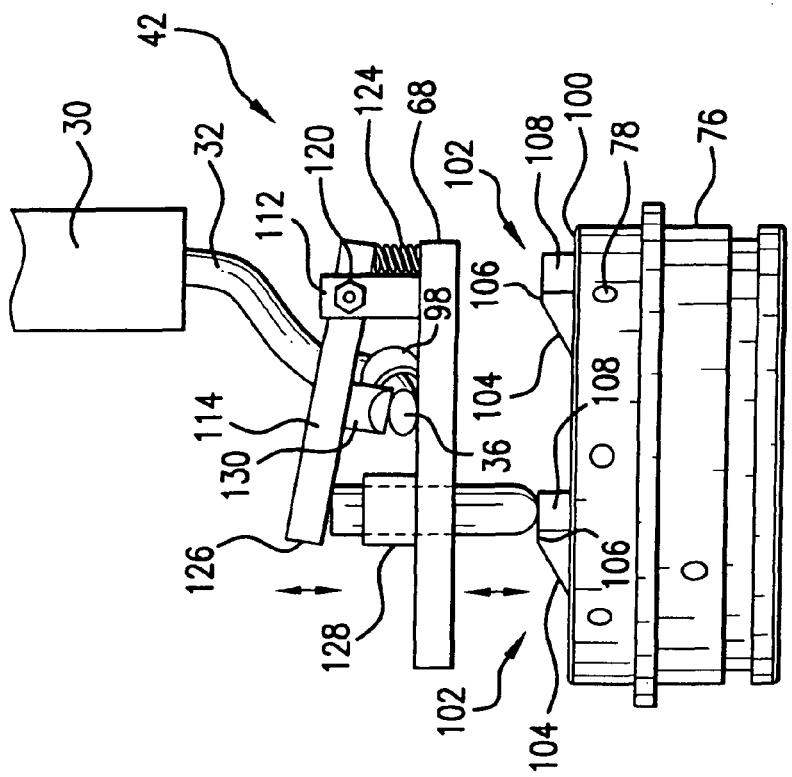
FIGS. 14A and 14B are schematic representations of the operation of the mechanism for control of the tube opening for controllable release of the biocide in the chamber surrounding the sensor.
Figure 14B:
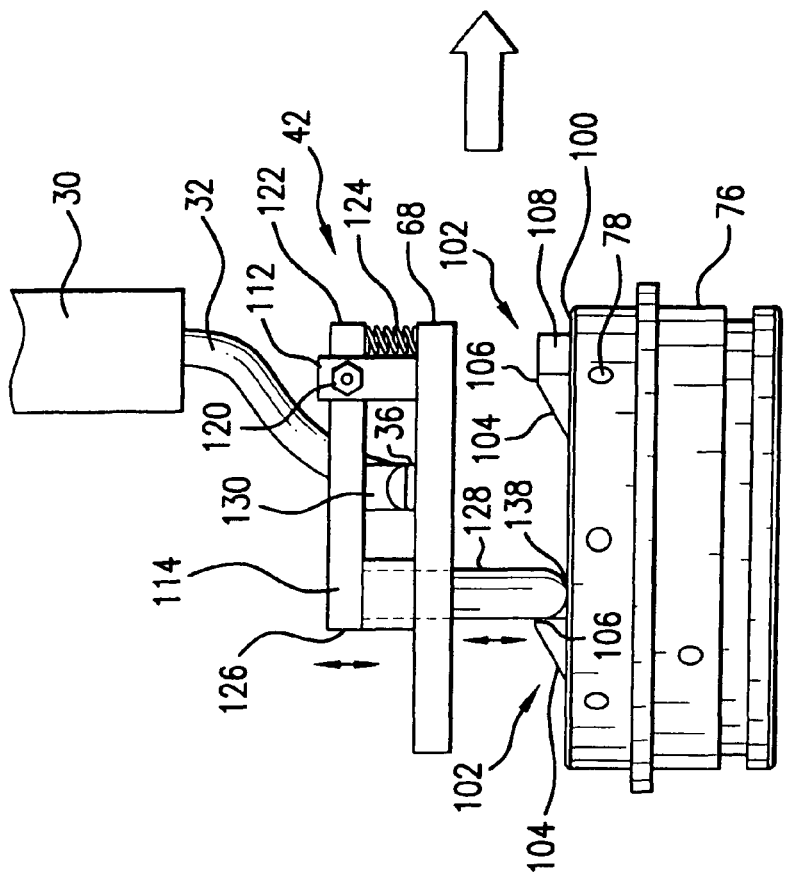

The reservoir 30 with biocide as best shown in FIGS. 4, 6, and 14A-14B is mounted within the housing 18, preferably on wall 64 of the inner cup 56 with a tube end 36 of the silicon tube 32 attached to the support disk 68 by any means known to those skilled in the art, including for example a loop 98 embracing the tube and attached to the disk 68 at a predetermined position, as shown in FIG. 14B.

As best shown in FIGS. 4, 5, 6 and 14A-14B, the chamber bulk-head 76 carries on the upper surface 100 thereof a plurality of ramp units 102 disposed circumferentially at the outer periphery of the chamber bulk head 76. As best shown in FIGS. 9A-9B and 14A-14B, each ramp unit 102 includes a ramp portion 104, a horizontal top portion 106, a void portion 108 cut off abruptly from the horizontal top portion 106, and an opening 110 passing through the entire height of the ramp unit 102. Each ramp unit 102 is secured to the upper surface 100 of the bulkhead 76 by a fastener (not shown) inserted into the opening 110.

The pinch valve mechanism 42 is mounted at the top surface of the support disk 68. The pinch valve 42 includes a pivot post 112, best shown in FIGS. 10 and 14A-14B, which is attached at the bottom thereof to the surface of the support disk 68 and extends vertically therefrom to pivotally receive a lever arm 114 (best shown in FIGS. 11 and 14A-14B) between two supports 116 and 118 and is attached thereto by a fastener 120. At the end 122 thereof, the lever arm 114 is coupled to the upper surface of the support disk 68 by a resilient element 124, such as a spring. At the other end 126 the lever arm 114 is in pressing relationship with the push rod 128 (best shown in FIGS. 13 and 14A-14B) which reciprocates vertically through an opening in the support disk 68.

Between the pivoting point 120 and the end 126 of the lever arm 114, there is attached a pinch tip 130 (best shown in FIGS. 12A-12B and 14A-14B). The pinch tip 130 is attached to the lever arm 114 by a fastener (not shown) threaded into the opening 132 of the pinch tip 130. The pinch tip has a pressing rib 134 formed between two cut off sides 136 for the purposes of controlling the opening of the tube end 36 of the silicon tube 32 as will be presented further herein.

The tube end 36 is attached to the surface of the support disk 68 for example by the loop 98 (shown in FIG. 14B), so that, as best shown in FIG. 14A, when the push rod 128 is in the void 108 of the ramp unit 102, or is between the ramp units 102, the resilient element 124 pushes the end 122 of the lever arm 114 from the support disk 68, thus keeping the lever arm 114 in a horizontal position with the pinch tip 130. The pressing rib 134 presses onto the tube end 36 of the silicon tube 32 thereby closing the same, as presented in FIG. 14A.

When the inner cup is rotated relative to the outer cup by means of rotating the support disk 68 by the motor 82, the lower portion 138 of the push rod 128 climbs up along the ramp portion 104 of the ramp unit 102 thereby causing the push rod 128 to move vertically through the support disk 68 which lifts the edge 126 of the lever arm 114. This action causes the gradual lifting of the pinch tip 130, specifically the pressing rib 134 above the surface of the support disk 68. This releases the pressure of the pressing rib 134 on the tube end 36 to result in the gradual opening of the tube end 36 until the tube end 36 is completely opened, as best shown in FIG. 14B. At this time, the resilient element 124 is pressed down by the end 122 of the lever arm 114 to accumulate the resilient energy in the resilient element 124.

When the supporting disk 68 is further rotated counter-clockwise relative to the bulk-head 76, a relative displacement of the push rod 128 with regard to the ramp unit 102 is attained. Specifically when the lower portion 138 of the push rod 128 has moved from the horizontal portion 106 to the void portion 108 of the ramp unit 102, the push rod 128 reciprocates down into the void 108, whereby the lower portion 138 of the push rod 128 reaches and is pressed against the surface of the support disk 68. At this time the end 126 of the lever arm 114 lowers down to the central portion 140 of the push rod 128 between the elements 142 and 144. This action is caused by the resilient element 124 which releases the energy which has been accumulated.

The lever arm 114, actuated by the resistant element 124, disposes itself in horizontal relationship with the support disk 68, thereby lowering the pressing rib 134 of the pinch tip 130 and closing the tube end 36, as shown in FIG. 14A.

It is clear that by displacing the support disk 68, e.g. the inner cup 56 relative to the outer cup 58 mounted on the chamber bulk head 76, the tube end 36 of the silicon tube 32 is controllably transferred between the closed and open states depending on the position of the lower portion 138 of the pinch tip 130. The control of the release of the biocide 28 from the reservoir 30 into the chamber 20, is thus performed in complete synchronization with the sampling cycle of the autonomous device 10 and in synchronization with opening/closing of the chamber 20.

By controlling the steepness of the ramp portion 104 of the ramp units 102, gradual opening of the tube end 36 from the completely closed position (shown in FIG. 14A) to the completely open position (shown in FIG. 14B), may be attained. In this manner the control of the release of the biocide 28 from the reservoir 30 through the silicon tube 32 may be controlled through programmed actuation of the motor 82 in accordance with the program embedded in the programmable microprocessor 16 prior to the deployment of the autonomous device 10 of the present invention.

It is to be noted, that the inner cup 56 and the stirrer 94 may rotate in either direction, clockwise or counter-clockwise. The biocide dispensing may be accomplished only when the inner cup 56 rotates in one direction, for example, counter-clockwise for the present embodiment shown in FIGS. 14A-14B. However, the ability of the reverse rotation for the inner cup is important for the operation of the device 10 in the event of the cup motion obstruction. During the reversed (clockwise) rotation of the inner cup 56, the push rod 128 pushes the ramp unit 102 out of the way. However, when the inner cup resumes its rotation in the "normal" direction (counter-clockwise), then the ramp unit 102 returns to its intended position.

Referring again to FIG. 7, the outer cup 58 may be provided with sediment escape channels 63 which, for example, may extend from the bottoms of the opposite outer cup openings 62 to the end 50 of the outer cup 58, although other shapes of the channels 63 are also contemplated in the present device. The channels 63 facilitate removal of sediments which may accumulate between the inner and outer cups.

Referring again to FIGS. 1, 3A and 5, the autonomous device 10 includes a power and communication plug 150 which is a submersible and wet mattable plug, meaning it may be plugged in under the water. The power and communication plug 150 has a Y-connector which has one end thereof extending from the plug to the sensor instrument 54 to supply power and communication thereto, while the other end of the Y-connector is able to receive power from an external supply and to provide communication for external control (the user interface for PC programming in the lab prior to deployment), or to function to telemetry data to the remote telemetry and data collection system.

The housing 26, which is coupled to the sensor housing 18, serves as mechanics, electronics and battery casing and may receive batteries 152 (shown in FIG. 4) therein, as well as the drive motor 82, gear train 84, limit switch cams 86, or the optical encoder 156 and the encoder disk 158. Also, the housing 26 accommodates a second motor 90 and a printed circuit board 154 (shown in FIG. 5) with the programmable microprocessor 16 and the non-volatile memory 46 providing that all electrical, electronic and mechanical components of the autonomous device 10 are kept within the housing 26 sealed from water intrusion.

Figure 15:
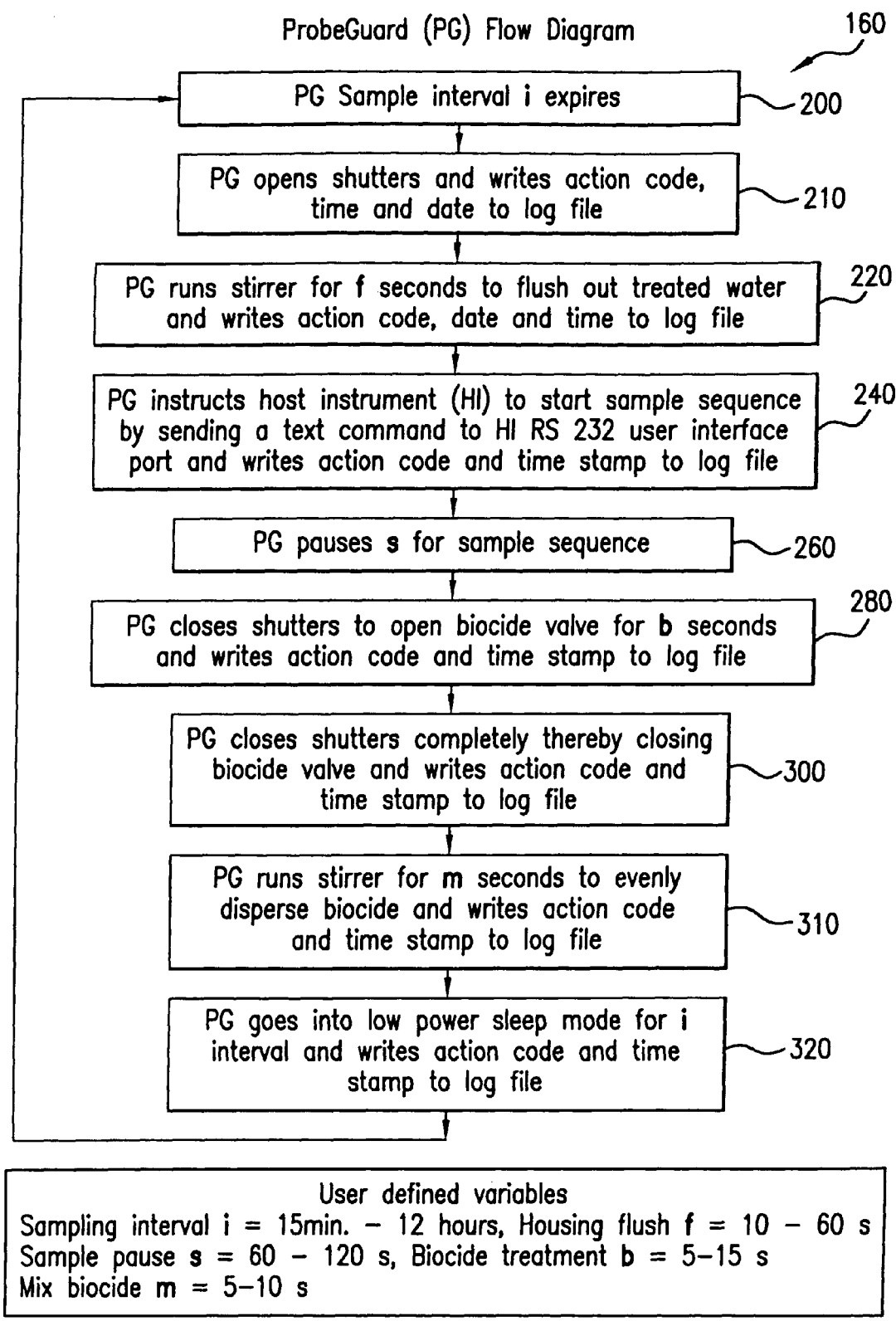
FIG. 15 is a flow-chart diagram of the software embedded in the microprocessor in the monitoring device of the present invention.

Referring to FIG. 15, the sequence of operations of the autonomous device 10 controlled by the programmable microprocessor 16 is presented as follows. The programmable microprocessor 16 has software 160 embedded therein which synchronizes the operation of all parts of the autonomous device 10 to run the sampling cycle of the sensors 14 in a predetermined order and in complete synchronization with mechanical motion of the inner cup versus outer cup, as well as in synchronization with the release of the biocides from the reservoir 30 into the chamber 20.

As presented in FIG. 15, when a previous sample interval "i" expires in block 200 (the inner cup openings 60 are closed by the wall portion of the outer cup 58 between the outer cup opening 62 as shown in FIG. 8A), the microprocessor 16 issues an instruction for the autonomous device 10 to pass the logic to block 210 in accordance with which the inner cup 56 assumes the position with relation to the outer cup 58 where the inner cup opening 60 and outer cup opening 62 overlap, as presented in FIG. 8B, to open the chamber 20 to the ambient environment to the fullest extent. At this position, the logic of the microprocessor 16 writes the action code, time and date to a log file.

Further the information or logic passes to block 220 where with the completely opened chamber 20, the microprocessor 16 instructs the motor 90 to actuate the stirrer 94 for "f" seconds to flush out water contained in the chamber 20. In block 220, the microprocessor 16 writes the action code, date and time of the action to the log file.

By the motion of the stirrer 94, the water contained in the chamber 20 before the shutters were opened in block 210, is completely replaced with the fresh water from the aquatic environment 12. Rotational movement of the stirrer 94 when the windows of the chamber 20 are opened creates rotational flow, e.g. the turbulence, resulting in pushing the water from the chamber with following bringing in of the fresh water into the chamber. The stirrer works for a predetermined time duration, for example 10-60 seconds, to replace water in the chamber 20.

Upon completion of the stirring action, the logic flows to block 240 and the microprocessor 16 instructs the sensor instrument 54 to start a sample sequence sending a text command to post instrument, e.g. RS232 user interface port, and writes action code and time stamp to the log file. The microprocessor 16 instructs the entire system to pause for "s" seconds, for example 60-120 seconds, to complete the sample sequence in block 260.

Upon the sample sequence (sampling time period) being completed, the microprocessor 16 activates block 280 and instructs the motor 82 to close the chamber 20 to the extent sufficient to open biocide valve mechanism 42 for "b" seconds (for example 5-15 seconds). During this action, the microprocessor 16 writes action code and time stamp to the log file. When the biocide valve 42 opens the tube end 36 as presented by FIG. 14B, the biocide 28 is released from the reservoir 30 by a gravity assist flow presented in previous paragraphs, and the logic moves to block 300 where the microprocessor 16 instructs the motor 82 to close shutters (inner and outer cup openings) thereby completely causing the pinch valve mechanism 42 to close the tube opening 36, as shown in FIG. 14A, and writes action code and time stamp to the log file.

At this time, the chamber 20 contains an anti-fouling environment created by releasing the biocide from the reservoir 30 and diluting it in the water in the chamber 20. Further, the microprocessor 16 instructs the motor 90 to run the stirrer 94 for "m" seconds (for example 5-10 seconds) as instructed in the logic block 310. By rotating the stirrer 94 in the chamber 20 containing the anti-fouling environment (e.g. the biocide diluted in the water), the biocide is evenly dispersed in the chamber 20 to immediately surround the surface of the sensors 14 and to "sterilize" the environment surrounding the sensors 14. In block 310, the logic writes the action code and time stamp to the log file.

The logic further flows to block 320 where the microprocessor 16 instructs the autonomous device 10 to cease operation for a predetermined "sleep" time interval "i" (15 minutes through 12 hours) and writes the action code and time stamp to the log file. Upon the "sleep" mode being completed, the logic loops back to block 200 and the process repeats through blocks 210 through 320.

Although the autonomous device 10 is sensor independent, meaning that any kind of environmental sensor can be used therewith, the sensors envisioned in the scope of this invention may include sensors basically for all environmental measurements such as, for example, optical sensors for measurement of oxygen, chlorophyll, pH, fluorescence sensors, sensors for measuring temperature, salinity, etc.

The present device may use a wide variety of biocide salts including calcium, hydrochloride in the form of pellets or powders. Copper fluoride is also one of the choices for the biocide as it is highly soluble in water and forms a very dense solution. As has been presented in previous paragraphs, up to four separate biocide reservoirs may be used in the autonomous device positioned in such a way that the tube ends thereof may be opened simultaneously by respective pinch valves 42. Alternatively, each biocide reservoir may be opened or closed in a programmable manner in a specific sequence with regard to other biocide reservoirs to provide for a great flexibility in dosing the water in the chamber in a predetermined desired manner.

Although this invention has been described in connection with specific forms and embodiments thereof, it will be appreciated that various modifications other than those discussed above may be resorted to without departing from the spirit or scope of the invention as defined in the appended claims. For example, equivalent elements may be substituted for those specifically shown and described, certain features may be used independently of other features, and in certain cases, particular applications of elements may be reversed or interposed, all without departing from the spirit or scope of the invention as defined in the appended claims.

What is claimed is:

1. A device with bio-fouling control for autonomous monitoring of a fluid environment, comprising:

at least one sensor unit operationally controllable to operate in accordance with a predetermined sampling cycle, said sampling cycle including at least one sampling time period followed by an anti-fouling treatment time period, a sensor envelope positioned in a surrounding relationship with said at least one sensor unit and defining a chamber containing said at least one sensor unit, said sensor envelope having at least one window formed therein, at least one source of an anti-fouling matter, and a control unit operatively coupled to said sensor envelope and said at least one source of the anti-fouling matter, wherein said control unit actuates said sensor envelope to control opening and closing of said at least one window formed therein to provide fluid communication between said at least one sensor unit and a fluid to be sampled within said chamber during said at least one sampling time period, and further activates said at least one source of the anti-fouling matter to create an anti-fouling environment in said chamber during said anti-fouling treatment time period.

2. The device of claim 1, wherein said at least one source of the anti-fouling matter includes a reservoir containing a biocide matter and a tube coupled at one end thereof to said reservoir, and having another end in controlled fluid communication with said fluid in said chamber, wherein during said anti-fouling treatment time period said biocide matter is controllably released into said chamber to dissolve in said fluid within said sensor envelope, thereby forming said anti-fouling environment surrounding said at least one sensor unit.

3. The device of claim 2, wherein said at least one window is opened under control of said control unit during said at least one sampling time period to permit said fluid inside said sensor envelope in contact with said at least one sensor unit, and wherein said at least one window is controllably closed during said anti-fouling treatment time period to maintain said anti-fouling environment inside said sensor envelope.

4. The device of claim 3, wherein said control unit synchronizes opening/closing of said at least one window with said controllable release of said biocide matter in said chamber.

5. The device of claim 3, wherein said sensor envelope includes an outer cup and an inner cup positioned in concentric relationship with said outer cup, said outer cup having an outer cup wall and a plurality of outer cup openings formed at predetermined positions on said outer cup wall, and said inner cup having an inner cup wall and a plurality of inner cup openings formed at predetermined positions on said inner cup wall, said inner and outer cups having a first relative disposition during said at least one sampling time period and a second relative disposition during said anti-fouling treatment time period, wherein in said first relative disposition between said inner and outer cups, respective ones of said plurality of inner cup openings and of said plurality of outer cup openings are positioned to overlap each other, and wherein in said second relative disposition between said inner and outer cups, said respective inner cup and outer cup openings are displaced each from the other in a controlled manner.

6. The device of claim 5, wherein during said anti-fouling treatment time period, said displacement between said respective inner cup and outer cup openings is synchronized with the release of said biocide matter by said control unit.

7. The device of claim 5, further comprising an actuation unit operatively coupled to either of said inner and outer cups to establish a respective one of said first and second relative dispositions therebetween in accordance with instructions received from said control unit.

8. The device of claim 1, wherein said control unit further includes a microprocessor preprogrammed prior to deployment of said device in said fluid environment.

9. The device of claim 1, further comprising a non-volatile memory, wherein data obtained from said at least one sensor unit is stored in said non-volatile memory under control of said controller, said data being dispatched periodically from said non-volatile memory to a telemetry and data collection system via a communication link established between said device and the telemetry and data collection system.

10. The device of claim 1, wherein said device further includes an interface port to communicate with a host computer for control of said device during the deployment thereof.

11. The device of claim 2, wherein said biocide matter includes at least one salt selected from a group consisting of: calcium hypochlorite pellets, calcium hypochlorite powder, copper chloride, salts of acids, metal salts, dry chemicals, water soluble chemicals.

12. The device of claim 5, further comprising:

a first and second co-axial supporting disks positioned in said chamber and rotationally displaceable about an axis thereof, said first and second co-axial supporting disks being spaced each from the other along said axis, wherein said inner cup is mounted on said first supporting disk, and wherein said outer cup is mounted on said second supporting disk, a plurality of ramp units positioned circumferentially on a surface of said second supporting disk a predetermined distance each from another between said first and second supporting disks; and a valve mechanism mounted on said first supporting disk in a controllable contact with said another end of said tube of said at least one source of the anti-fouling matter, said valve mechanism being actuated by interaction with a respective one of said plurality of ramp units in accordance with a relative disposition between said first and second supporting disks to control opening of said another end of said tube when said first and second co-axial supporting disks are rotationally displaced under control of said control unit.

13. The device of claim 12, further comprising a flushing unit inside said chamber operating to remove said anti-fouling environment therefrom upon completion of said anti-fouling treatment time period prior to said at least one sampling time period.

14. The device of claim 12, further comprising:

a casing connected to said sensor envelope at one end thereof, said casing having an internal cavity fluidly separated from said chamber of said sensor envelope, batteries and an actuator mechanism received within said internal cavity of said casing, and wherein said controller is received in said casing.

15. A method for bio-fouling control of a device for monitoring a fluid environment, comprising the steps of:

forming a sensor envelope for at least one sensor unit, positioning said at least one sensor unit into a chamber defined within said sensor envelope, programming a control unit prior to deployment of the autonomous device in the fluid environment, deploying said autonomous device having said preprogrammed controller unit embedded therein in the fluid environment, opening said chamber to said fluid environment under control of said preprogrammed control unit to establish fluid communication between a fluid and said at least one sensor unit, sampling said fluid, upon completion of the sampling during at least one sampling time period, closing said chamber, and releasing, under the control of said preprogrammed control unit, at least one biocide matter in said chamber to create an anti-fouling environment therein, thereby exposing said at least one sensor unit to the anti-fouling environment during an anti-fouling treatment time period.

16. The method of claim 15, further comprising the steps of:

upon completion of said anti-fouling treatment time period, opening said chamber, and replacing said anti-fouling environment in said chamber with said fluid.

17. The method of claim 15, further comprising the step of:

during said anti-fouling treatment time period, activating stirring of said anti-fouling environment to evenly disperse said at least one biocide matter within said chamber.

18. The method of claim 15, further comprising the steps of:

recording data acquired during said at least one sampling period in a memory block of said autonomous device, establishing a communication link between said autonomous device and a data collection system, and sending said recorded data from said memory to said data collection system for further processing.

19. The method of claim 15, further comprising the steps of:

preprogramming said control unit prior to the deployment of said autonomous device to embed therein operation parameters selected from the group consisting of: sampling frequencies, biocide dispense time, biocide dispense amount, stirring duration of said biocide in said chamber, duration of flushing of said anti-fouling environment from said chamber, duration of said sampling time period, duration of said anti-fouling treatment time period, and parameters for synchronized operation of said autonomous device, and controlling said control unit from a host computer during the deployment if a re-programming is needed.

20. A device with a bio-fouling control for monitoring a fluid environment, comprising:

at least one sensor unit operating in accordance with a predetermined sampling cycle including at least one sampling time period followed by an anti-fouling treatment time period, a sensor envelope for said at least one sensor unit, said at least one sensor unit being disposed in a chamber defined by said sensor envelope, at least one biocide reservoir containing a biocide matter in controlled communication with said chamber, an actuating unit operatively coupled to said at least one biocide reservoir, and a control unit controlling said actuating unit in a programmable manner, and operatively coupled to said sensor envelope to controllably open and close said chamber, wherein, during said anti-fouling treatment time period, upon completion of said at least one sampling time period, said control unit closes said chamber, and said actuating unit, under the control of said control unit, activates release of said biocide matter from said at least one biocide reservoir in a controlled fashion through a density gradient mechanism to create an anti-fouling environment in said closed chamber, thereby exposing said at least one sensor unit to said anti-fouling environment upon completion of said at least one sampling time period to substantially prevent and eliminate bio-fouling in immediate surrounding of said at least one sensor unit, wherein said anti-fouling environment includes a fluid sample retained within said chamber until displaced by a subsequent fluid sample.

\* \* \* \* \*